United States Patent [19]

Gregory

[11] 4,376,376

[45] Mar. 15, 1983

[54] CRYOGENIC DEVICE OPERABLE IN SINGLE OR DUAL PHASE WITH A RANGE OF NOZZLE SIZES AND METHOD OF USING THE SAME

[75] Inventor: Harold D. Gregory, West Covina, Calif.

[73] Assignee: Virginia M. Gregory, West Covina, Calif.

[21] Appl. No.: 148,828

[22] Filed: May 12, 1980

[51] Int. Cl.³ .............................................. A61B 17/36
[52] U.S. Cl. ........................................... 62/51; 62/50; 62/293; 62/514 R; 128/303.1
[58] Field of Search ...................... 128/303.1, 399, 400; 62/51, 293, 50, 514 R; 222/3

[56] References Cited

U.S. PATENT DOCUMENTS

3,702,114 11/1972 Zacarian ...................... 128/303.1 X
4,292,973 10/1981 Yamauchi et al. ................. 128/303.1

*Primary Examiner*—Michael H. Thaler
*Attorney, Agent, or Firm*—Sellers and Brace

[57] ABSTRACT

A cryogenic device and a method for selectively dispensing a jet of gas or a mixture of gas and liquid cryogen particles, that is, single phase or two phase fluid, at the user's option, from a nozzle selected from a range of nozzle sizes. Pressurized liquid cryogen is supplied through an orifice to a nozzle-equipped expansion chamber also connected to a pressure regulated source of gas. A valve-controlled passage venting to the atmosphere from the expansion chamber is normally closed but, when open, is effective to reduce the chamber pressure by a major fraction of 1 psig provided the gas flow from the pressurized gas source is interrupted. The single phase gas jet dispensed in the non-venting mode substantially instantly converts to a stable two phase jet of gas and liquid particles irrespective of which one of the nozzle sizes is then in use. If the liquid cryogen pressure falls during the use of a larger nozzle, the pressure is quickly re-established by briefly admitting gas from the pressure regulated source via the expansion chamber and back flow into the liquid supply.

23 Claims, 3 Drawing Figures

CRYOGENIC DEVICE OPERABLE IN SINGLE OR DUAL PHASE WITH A RANGE OF NOZZLE SIZES AND METHOD OF USING THE SAME This invention relates to cryogenic devices, and more particularly to an improved and unique spraying device and method utilising liquid cryogen flowing at a rate within a range of flow rates and convertible at each rate substantially instantaneously between single phase and dual phase flow at the user's option.

BACKGROUND OF THE INVENTION

In general, cryogenic devices fall within one of two categories, namely, those utilizing high pressure gas to produce low temperatures by the Joules-Thompson phenomena and the second utilizing liquid cryogen which vaporizes extremely rapidly at room temperature and pressure. Joules-Thompson equipment typically utilizes gas stored at 500 to 800 psi which is expanded to atmospheric pressure in close proximity to tissue to be necrotized. Such equipment requires adequate safeguards to protect the patient and operator against the hazards associated with these high pressures. Cryogenic devices using liquid cryogen typically operate at relatively low pressures of about 1 atmosphere and can apply a spray of finely divided liquid cryogen directly to the surface to be necrotized, or to the interior of a probe, in each instance utilizing the latent heat of evaporation in a highly effective and efficient manner. Spray devices using liquid cryogen are much faster, particularly when freezing tissue to depths in excess of one or two millimeters. An adequate supply of cryogen can be stored in a small heat insulated container readily held and manipulated in the operator's hand.

Various devices designed for liquid cryogen heretofore proposed are subject to numerous disadvantages avoided by this invention. Typical U.S. Pat. Nos. disclosing liquid cryogenic devices include Nelson 1,659,663; Posch 2,645,097; Johnston 3,220,414; Leigh 3,298,371; Bryne 3,534,739, 3,651,813, 3,712,306; Zacarian 3,702,114; Reynolds 3,739,956; Kollner 3,794,039; Tromovich 3,823,718. No one of these devices can selectively dispense single or a two phase jet of cryogen at the user's option. Single phase and two phase jets have distinctly different cooling capacities and fields of usefulness. A cryogenic device providing the selective choice of single or two phase jets is disclosed in my co-pending application for United States Letters Patent, Ser. No. 936,909, filed Aug. 25th, 1978, now abandoned. That device is instantly convertible between single and dual phase operation by manipulation of a single control means when equipped with any one of a limited range of relatively small diameter dispensing nozzles, that is, nozzles having a diameter of $v = 0.015$ inches, approximately, or less.

SUMMARY OF THE INVENTION

This invention avoids the shortcomings of prior proposals for utilizing liquid cryogen to produce sub-freezing temperatures, and very substantially extends the range of nozzle sizes usable in the same device without loss of the selective single phase-dual phase capability. The liquid cryogen stored in a hand held Dewar is supplied through an orifice into an expansion chamber provided with a quick release nozzle mounting and a manually operable vent to the atmosphere. A range of nozzle sizes can be quickly secured in this mounting. Instantaneous conversion between single phase and dual phase cryogen flow issuing from any one of these nozzles is achieved by effecting a small range pressure change in the expansion chamber. This change is accomplished, in part, by operating the valve of the vent passage connecting the expansion chamber to the atmosphere and, in part when a larger nozzle is in use, by momentary introduction of pressurized gas into the expansion chamber from a pressure regulated gas source. When the venting passage is closed, only a jet of single phase gaseous cryogen issues from the nozzle. With the venting passage open, the pressure in the expansion chamber drops by a major fraction of 1 psig and a dual phase jet of cryogen issues from the nozzle. When a large nozzle at the upper end of the range of nozzle sizes is present, single phase discharge from the nozzle is assured by maintaining a pressure level in the expansion chamber to limit the admission of liquid from the Dewar. The single phase flow is substantially instantly convertible to dual phase flow by opening the venting passage and closing or substantially cutting off the flow of pressurized gas to the expansion chamber. If the dual phase flow tends to become unstable when using larger nozzles, for example, tends to carry slugs of liquid instead of evenly distributed fine particles, tends to pulse, tends to fluctuate between single phase and dual phase, is non-uniform, it is quickly stabilized simply by momentary release of the manual control to increase the flow of pressurized gas from the gas source. After one or two seconds, fully stable conditions are restored and the control is operated to resume two phase flow.

Accordingly, it is a primary object of this invention to provide an improved cryogenic apparatus and method of selectively dispensing a single phase or a dual phase jet of cryogen using any one of a wide range of nozzle sizes.

Another object of the invention is the provision of cryogenic apparatus and a method of instantly converting between single phase gas flow and dual phase gas and liquid particle flow in a highly stable and uniform manner.

Another object of the invention is the provision of a hand-held readily manoeuvreable cryogenic device having a self contained supply of liquid cryogen in communication with a pressure regulated gas supply so constructed and arranged as to dispense a single phase gas jet or a dual phase gas and liquid particle jet from any one of a series of nozzle sizes chosen from an extended range of sizes.

Another object of the invention is the provision of a cryogenic device employing a Dewar charged with liquid cryogen connected to a nozzle-equipped expansion chamber and a source of pressure regulated gas and means to control the gas pressure in the expansion chamber and the Dewar.

Another object of the invention is the provision of a cryogenic surgical unit in which the selective spraying of single phase gas or dual phase gas and liquid particles is controlled by means including a source of gas, preferably a cryogen, under pressure separate and distinct from the source of liquid cryogen.

These and other more specific objects will appear upon reading the following specification and claims and upon considering in connection therewith the attached drawing to which they relate.

Referring now to the drawing in which a preferred embodiment of the invention is illustrated:

Figure 1:
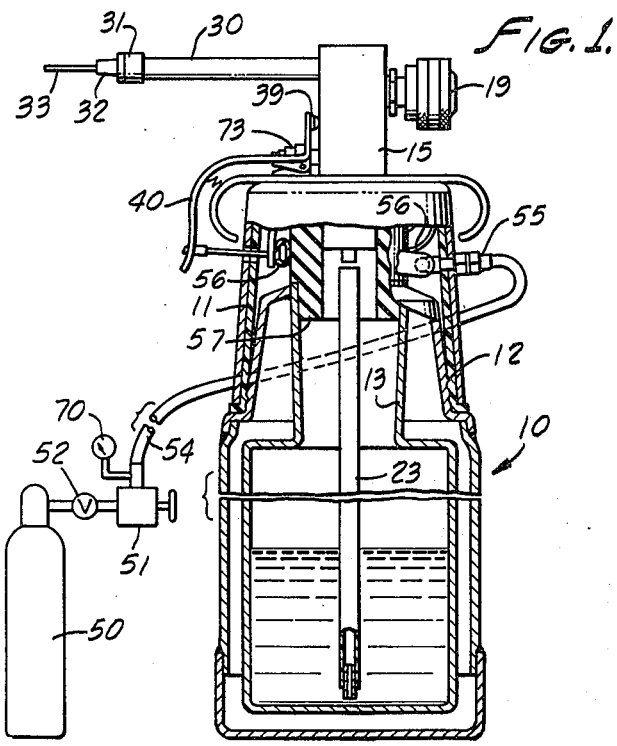
FIG. 1 is an elevational view of an illustrative embodiment of the invention with portions broken away and in cross section to show structural details.
Figure 3:
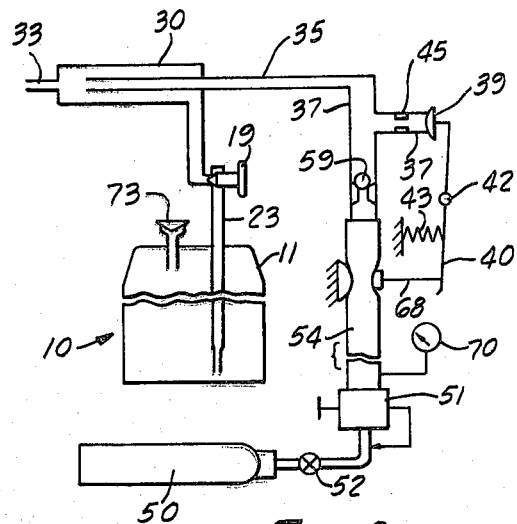
FIG. 3 is a diagrammatic view of the construction shown in FIG. 1.
Figure 2:
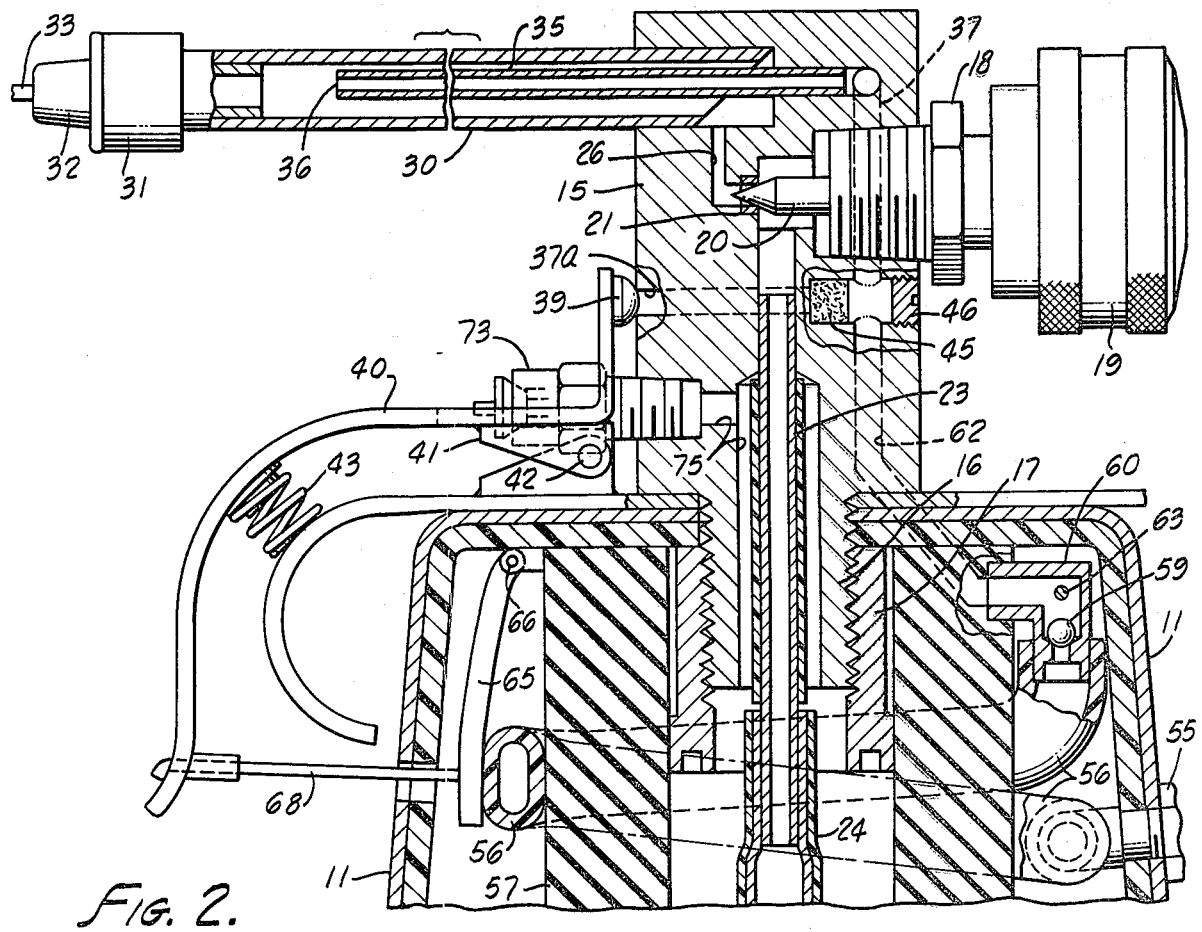
FIG. 2 is a cross sectional view on an enlarged scale taken through the upper portion of FIG. 1.

Referring to FIGS. 1 to 3, there is shown a Dewar 10 provided with a removable heat insulated cap 11 having threads 12 mating with corresponding threads on the filling inlet 13 of the Dewar. Substantially all operating components of the cryogenic device are mounted on cap 11. These include a body member 15 having a threaded shank 16 extending through the top of cap 11 and held assembled thereto by a sleevelike nut 17. A cryogen flow control valve 18 is threaded into member 15 and is provided with a control knob 19 for a needle valve element 20 which cooperates with seat 21 to provide a flow control orifice. Liquid cryogen is supplied to the inlet side of valve 20 by a delivery tube 23 extending downwardly to a point near the bottom of the Dewar and preferably shrouded with heat insulating material 24. The flow control orifice discharges into a delivery passage 26 opening into an expansion chamber 30 mounted in body member 15 and provided at its outer end with a female luer fitting 31 detachably seating the male fitting 32 of a cryogen dispensing nozzle 33 in a manner well known to persons skilled in this art. Expansion chamber 30 is preferably made of metal or glass; while its size may vary a chamber approximately 3 inches long and ¼ inch internal diameter functions satisfactorily.

Expansion chamber 30 is vented to the atmosphere by way of tube or passage 35 which may be about ⅛ inches in internal diameter for its inlet end 36 opening into the expansion chamber and its other end opening into an L-shaped passage 37 in member 15. The outlet end of this passage opens through the wall of member 15 at 37a and is normally closed by a manually operable venting valve 39 mounted on the upright leg of an L-shaped operating lever 40. A bracket 41 secured to the horizontal leg of lever 40 is pivoted to the Dewar cap by pivot pin 42 and pivotally mounts the lever 40 for movement of valve 39 between open and closed positions. A spring valve 43 normally maintains valve 39 closed and seated over the outlet end of passage 37.

The gas venting passages 35, 37 serve the important function of lowering the pressure in the expansion chamber by a major function of one psig when valve 39 is open. The extent of the pressure reduction can be controlled in various ways but, as herein shown, is accomplished by a passage restrictor 45 of brass wool compacted by trial and error to provide the desired flow restriction and pressure reduction. This wool is inserted through an opening in body member 15, which opening is normally closed by the removable fluid-tight threaded plug 46.

Pressurized gas is conveniently supplied to expansion chamber 30 from the bulk storage tank 50 via an adjustable pressure regulator 51, a cut-off valve 52, and hose 54 connected to a fitting 55 mounted on Dewar cap 11. The gas then flows through a flexible tubing 56 encircling a soft rubber stopper 57 bonded or otherwise fixed to the bottom of the Dewar cap 11 and then passes through a check valve 59 mounted in an elbow fitting 60 and into passage 62 connected to venting passage 37 through which it passes into the expansion chamber 30.

A pin 63 extends across the elbow fitting 60 to retain check ball 59 captive adjacent its seat in stopper 57.

The flow of pressurized gas from tank 50 into the expansion chamber is regulated or controlled by collapsing the wall of tubing 56 against the outer wall of stopper 57 by a pressure pad 65 having its upper end pivotally connected to the interior of the Dewar cap by pivot pin 66. A flexible rod 68 extends between pressure pad 65 and a fixed connection to the lower end of the venting valve operating lever 40. Accordingly, when lever 40 is pivoted counter-clockwise, as shown in FIG. 2, to open the venting valve 39, pressure pad 65 collapses tubing 56 to reduce or block the flow of pressurized gas from tank 50 to expansion chamber 30.

Dewar 10 is provided with a pressure relief valve 73 mounted in the sidewall of member 15 and in communication with the interior of the Dewar via a passage 75 extending through member 15 above its threaded shank. Typically, relief valve 73 is calibrated to open at 10 psig, that is a pressure somewhat above the normal operating pressure of the cryogenic device.

OPERATION

To place the cryogenic device into operation the operator removes cap 11 and pours into Dewar 10 a quantity of liquid cryogen, such as liquid nitrogen. The cap is then restored to its assembled position with stopper 57 extending into and snugly seated against the inlet of filling opening 13.

The gas tank 50, which is to deliver only gas, is charged with the same cryogen as the Dewar, either in liquid or gas phase. However, tank 50 may contain a charge of a different cryogen, or even air, since only the gaseous phase is bled from the top of the tank and conducted to expansion chamber 30. When the cryogenic device is not in use, valve 52 at tank 50 is closed and needle valve 19, 20 at the top of the Dewar is also closed.

Before placing the cryogenic device in use with one of the larger sizes of nozzles 33 requiring gas from tank 50 to initiate dual phase jetting of cryogen, the operator determines that pressure regulator 51 is properly adjusted to pressurize the expansion chamber to a pressure of about 9.2 psig. This is done by opening gas valves 20 and 52 and adjusting regulator 51 until his ear, held close to the Dewar, detects gas bubbling through the liquid in the Dewar. If the regulator is passing gas at an excessive pressure level, the pressure relief valve 73 will open and vent gas to the atmosphere. When the regulator has been properly adjusted, the bubbling of gas through the liquid will cease and the operator is assured that both the Dewar and the expansion chamber are properly stabilized at 9.2 psig. Typically, the outlet pressure at the regulator will be about 15 psig.

Typically and by way of illustration, nozzle 33 comprises one of a range of sizes of hypodermic needles modified by having their sharpened end cut off in a diametric plane. Such nozzles, or the like, and nozzles which are not needles are the full equivalent, have bore diameters ranging from 0.010 inches to 0.045 inches, function equally satisfactorily to dispense a jet of either single phase or dual phase cryogen when the expansion chamber is connected to the auxiliary supply of pressurized gas from tank 10 although the auxiliary gas supply is not necessary when using nozzles at the lower end of the size range.

In "A" of Table 1 are tabulated expansion chamber pressures with nozzles of different diameters under No Flow conditions, meaning "no flow through the nozzle". The expansion chamber and Dewar pressure is then stabilized at the same value and the cryogen gas is saturated. Nozzles ranging in size from 0.010 inches to 0.045 inches are arranged in order across the top line of "A". The second line of "A" lists the saturated gas pressure in the Dewar with the auxiliary gas valve 52 closed, valve 19, 20 fully open, valve 39 closed and while the flow from nozzle 33 is blocked.

gas through the liquid in the Dewar, and may even hear cryogen gas escaping from the pressure relief valve 73. In either event, the operator then lowers the pressure regulator adjustment until no gas escapes from valve 73 and he hears no bubbling of gas through the liquid cryogen. Tests disclose that the pressure then typically prevailing in the expansion chamber is about 9.2 psig and that only single phase cryogen is dispensed from the full range of the listed nozzle sizes so long as the venting

TABLE I

| A | Expansion Chamber Pressure Under No Flow Conditions | | | | | | |
|---|---|---|---|---|---|---|---|
| Nozzle Diameter | 0.010" | .015" | .021" | .033" | .035" | .041" | .045" |
| Nozzle Blocked And Vent Closed | 9.2 | 9.2 | 9.2 | 9.2 | 9.2 | 9.2 | 9.2 |
| B | Expansion Chamber Pressure Under Flow Conditions | | | | | | |
| Auxiliary Gas Vent Closed | 8.7* | 8.7* | 8.7* | 8.4** | 8.3** | 8.2** | 7.8** |
| | | | | Very unstable 2 Phase Flow | | | |
| Disconnected  Vent Open | 8.2** | 8.3** | 8.3** | 8.2** | 8.2** | 8.2** | 7.8** |
| C | | | | | | | |
| Auxiliary Gas Connected  Vent Closed Auxiliary Open*** | 9.2* | 9.2* | 9.2* | 9.2* | 9.2* | 9.2* | 9.2* |
| Vent Open; Auxiliary Closed | 8.2** | 8.3** | 8.3** | 8.2** | 8.2** | 8.2** | 7.8** |

*Single Phase Gas Cryogen
**Dual Phase Gas and Liquid Cryogen
*12-15 psig Regulator Setting Part "B" of Table 1 lists the pressure under "Flow" conditions for each of the nozzle sizes without any auxiliary gas. This can be accomplished either by closing the auxiliary gas valve 52 or by disconnecting hose 54 from fitting 55 (FIG. 1) whereupon the check valve 59 closes. No auxiliary gas can then enter the expansion chamber but can escape through nozzle 33 causing the expansion chamber pressure to drop to about 8.7 psig. The device now functions in a fully stabilized condition to dispense single phase cryogen with any nozzle size up to and including 0.021 inches. However, when the operator opens venting valve 39, the expansion chamber pressure drops to about 8.2 psig and the single phase flow is converted instantly to dual phase flow owing, it is believed, to the higher rate of flow of cryogen into the expansion chamber resulting from the increased pressure differential then prevailing across valve 20**.

However, if the operator endeavours to use nozzles larger than about 0.021 inches without the aid of auxiliary gas, part B of Table 1 shows the expansion chamber pressure drops to 8.2, or even to 7.8 psig with an 0.045 inch nozzle, even though venting valve 39 remains closed. Under these conditions the device dispenses a continuous dual phase spray of cryogen instead of single phase gas (as with the smaller nozzle) and the operator is unable to convert quickly between single and dual phase operation as is highly desirable and advantageous and as is possible when using the aforementioned smaller nozzles.

Part C of Table 1 shows the cryogen flow and expansion chamber pressure conditions when using an auxiliary source of pressurized gas. After a selected nozzle has been mounted in fitting 31, the operator opens the valve 52 to admit the pressurized gas, preferably cryogen gas of the same kind charged into the Dewar. He then fully opens the Dewar valve 20 and adjusts regulator 51 to raise the expansion chamber pressure to provide a blocking pressure to the flow of cryogen for the Dewar (8.75 as in Table C,) resulting in a steady single phase gas jet from nozzle 33. If the gas regulator outlet pressure is too high the operator will hear bubbling of valve 39 remains closed.

In further explanation, with small nozzles, (0.010 inches–0.21 inches) the pressure of boiling cryogen in the expansion chamber is sufficient to provide a back pressure to limit the flow of cryogen from the Dewar to such an extent that all cryogen in the expansion chamber becomes gas and only single phase gas jets from the nozzle. With a larger nozzle in place (0.033 inches–0.045 inches), however, in the absence of an auxiliary gas to pressurize the expansion chamber, the larger nozzle jetting a greater volume of the cryogen prevents the expansion chamber pressure from increasing to the same extent, and a greater volume of cryogen enters the expansion chamber from the Dewar all of which is not converted to gas. As a result the jet from the nozzle is dual phase. To obtain single phase flow with a larger nozzle in place a higher pressure is required than is provided by the boiling cryogen from the Dewar and this is provided by the auxiliary gas under pressure from tank 50.

Regulator outlet pressure indicated on guage 70 will be somewhat higher than the expansion chamber pressure to compensate for the pressure loss between the regulator and the expansion chamber. Typically, the regulator outlet pressure will range between 12-15 psig.

Conversion from single phase flow to a highly stable uniform flow of dual phase cryogen from any of these nozzles in the range from 0.010 to 0.045 inches inclusive is obtained substantially instantaneously by depressing the operating lever 40 to open venting valve 39 and to collapse flexible tubing 54 by pressure pad 65. Collapsing tube 54 cuts off the supply of auxiliary gas to the expansion chamber 30. Pressure tests show that the expansion chamber pressure then drops about 1 psig or more. When using nozzles larger than 0.021 inches and up to 0.045 inches it appears that a substantially increased flow of cryogen takes place from the Dewar into the expansion chamber and that a substantial portion of this liquid quickly vaporizes to provide a chamber pressure having the values set forth in the last line of Table 1 despite the substantially greater flow of cryogen issuing from the nozzle 33 and from the open venting valve 39.

After a period of dual phase flow from a nozzle larger than about 0.021 inches, the jet may tend to display a slightly unsteady characteristic. This is readily rectified by momentarily releasing and then again depressing the operating lever 40. This action serves to admit sufficient auxiliary gas from tank 50 to elevate the pressure in the expansion chamber, a portion of this gas under increased pressure back flowing past needle valve 20 into the Dewar through delivery tube 23. This back flow of warm gas bubbling through the liquid in the Dewar increases the rate of vaporization of the contracted liquid and a rapid restoration of the Dewar pressure results. It will, therefore, be recognized that repressurization of the Dewar reservoir occurs automatically whenever the expansion chamber pressure rises above the Dewar reservoir pressure.

While the particular cryogenic device operable in single or dual phase with a range of nozzle sizes herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

I claim:

1. A cryogenic device for selective operation to dispense either a jet of cryogen gas or a jet of gas and particles of liquid cryogen comprising:
a container for pressurized liquid cryogen having a nozzle-equipped expansion chamber adapted to be supplied with liquid cryogen therefrom;
means for supplying pressurized gas to said expansion chamber from a pressurized source and for venting gas from said expansion chamber to the atmosphere independently of gas flow through said nozzle, said means including operator-controlled means selectively operable to vary the gas pressure in said expansion chamber over a narrow range effective at the higher end of said pressure range to provide a flow of gas only from said nozzle and effective at the lower end of said range to provide a flow of a mixture of gas and liquid cryogen.

2. A cryogenic device as defined in claim 1 characterized by the provision of valve means between said expansion chamber and said container operable to close off the flow of liquid cryogen into said expansion chamber when said cryogenic device is not in use.

3. A cryogenic device as defined in claim 2 characterized in that said valve means between said expansion chamber and said container is operable to control the flow of liquid cryogen into said expansion chamber and the flow of gas from said expansion chamber into said container depending on the polarity of the pressure differential across said valve means.

4. A cryogenic device as defined in claim 1 characterized in that said manually operable means for varying the gas pressure in said expansion chamber includes means for opening said gas vent to the atmosphere and for controlling the flow of gas from said pressurized gas source into said expansion chamber.

5. A cryogenic device as defined in claim 4 characterized by the provision of back-flow control means in said means for supplying pressurized gas to said expansion chamber operable to close automatically and prevent the escape of gas from said expansion chamber to the atmosphere when said pressurized source of gas is detached from said expansion chamber.

6. A cryogenic device as defined by claim 5 characterized in that back-flow control means comprises a check valve movable to closed position by pressurized gas in said expansion chamber when said supply of pressurized gas is not in use.

7. A cryogenic device as defined in claim 1 characterized in that said device is selectively operable to provide single phase gas flow and two phase gas and liquid flow from cryogen dispensing nozzles ranging from 0.010 to 0.045 inches in diameter.

8. A cryogenic device as defined in claim 1 characterized in that all components except said means for supplying pressurized gas to said expansion chamber are interconnected in a unitary assembly adapted to be freely manoeuvred while held in one hand of an operator.

9. A cryogenic device as defined in claim 1 characterized in that said operator-controlled means for venting gas to the atmosphere and for supplying pressurized gas to said expansion chamber includes a single control manipulatable by the operator.

10. A cryogenic device as defined by claim 1 characterized in that said operator-controlled means includes means normally biasing said gas venting means closed.

11. In combination:
a Dewar chargeable with liquid cryogen;
means for delivering cryogen into an expansion chamber equipped with a readily detachable nozzle located exteriorly of said Dewar;
a pressure regulated source of pressurized gas connected to said expansion chamber;
manually controlled means for venting gas from said expansion chamber while simultaneously reducing substantially the flow of gas thereto from said pressurized gas source and effective in one of two normal operating positions thereof to provide single phase gas flow from said nozzle and to provide two phase gas and liquid particle cryogen flow from said nozzle in the other position thereof, irrespective of any size of nozzle between 0.010 and 0.045 inches in diameter.

12. The combination defined in claim 11 characterized in that said cryogen delivery means is operable at times to permit pressurized gas to flow from said expansion chamber into said Dewar as and when necessary to maintain substantially equalized pressure conditions in said expansion chamber and in said Dewar.

13. The combination defined in claim 12 characterized in that at least a portion of said expansion chamber is in heat exchange with the atmosphere whereby a pressure reduction in said expansion chamber occuring when operating with a larger size nozzle results in a slightly greater flow of liquid cryogen into said expansion chamber and the vaporization of a portion thereof thereby tending to augment the gas pressure while maintaining a two phase flow of gas and liquid cryogen particles from said nozzle.

14. That method of selectively dispensing a jet of cryogen in gaseous phase only and in a jet of gas and finely divided liquid particles at the user's option from any selected one of dispensing nozzles ranging in size from 0.010 to 0.045 inches in diameter which method comprises:
storing liquid cryogen in a Dewar under a predetermined pressure;

releasing liquid cryogen from said Dewar through an orifice into an expansion chamber in heat exchange with the atmosphere and equipped with means for mounting a selected one of said dispensing nozzles thereon;

providing said expansion chamber with means for venting gas therefrom to the atmosphere independently of said nozzle in an amount to lower the expansion chamber pressure less than about one psig and effective to convert a jet of single phase gaseous cryogen to a jet of dual phase gas and liquid cryogen particles when a nozzle of about 0.021 inches in diameter or smaller is in use;

providing said expansion chamber with a flow-controllable connection to a source of pressure regulated gas; and opening said gas venting means while reducing the flow of gas from said pressure regulated source when a nozzle larger than about 0.021 inches in diameter is in use and thereby effective to convert the jet of cryogen dispensed from said nozzle from single phase cryogen to two phase gas and liquid cryogen particles.

15. That method defined in claim 14 characterized in the step of closing said gas venting means and simultaneously restoring the flow of gas into said expansion chamber from said pressure regulated gas source when a nozzle of about 0.022 inches or larger is in use for as long as a few seconds and thereupon reopening said gas venting means and discontinuing the flow of gas from said pressurized source.

16. That method defined in claim 14 characterized in the step of briefly supplying gas from said pressure regulated gas source into said Dewar via said expansion chamber and said orifice thereby to quickly restore the pressure therein after the pressure has partially depleted after a period of use to dispense a two phase cryogen jet from a larger one of said nozzles.

17. That method defined in claim 14 characterized in the step of periodically and momentarily restoring the flow of gas into said expansion chamber from said pressure regulated source when using a nozzle of the larger range of sizes thereof thereby to raise the gas pressure in said expansion chamber and in said Dewar which gas pressure has become partially depleted by the greater flow of cryogen taking place when a larger size nozzle is in use to dispense a two phase cryogen jet.

18. That method defined in claim 14 characterized in the step of introducing pressurized gas from said expansion chamber into liquid cryogen in said Dewar when the pressure therein has fallen below said predetermined Dewar pressure thereby to restore the Dewar pressure to said predetermined pressure.

19. That method defined in claim 18 characterized in the step of bubbling said pressurized gas introduced from said expansion chamber through liquid cryogen in said Dewar thereby to expedite the vaporization of liquid cryogen and the restoration of said predetermined Dewar pressure.

20. A cryogenic device for selectively dispensing either a single phase or a dual phase jet of cryogen from nozzles of different diameters at the user's option comprising:

means for storing liquid cryogen at a predetermined minimum pressure;

an expansion chamber in communication with said pressurized cryogen via an expansion port;

means for detachably connecting any one of a plurality of nozzles to an outlet port of said expansion chamber and which nozzles have a port diameter ranging between 0.010 and 0.045 inches;

venting passage means for said expansion chamber equipped with a normally closed venting valve operable, when open, to reduce the pressure in said expansion chamber by a major fraction of one pound;

adjustable means for regulating the flow of pressurized gas to said expansion chamber from a pressure regulated source thereof; and manually operable means to open said venting valve and to interrupt the flow of gas from said pressure regulated source to said expansion chamber and thereby substantially instantly convert the jet dispensed from the one of said nozzles then in use from single phase gas to two phase gas and liquid cryogen particles.

21. A cryogenic device as defined in claim 20 characterized in that said pressure regulated gas source includes means for manually adjusting the pressure on the outlet side thereof to a predetermined pressure suitable for use with a selected one of said nozzle sizes.

22. In a cryogenic device:

a container for normally pressurized liquid cryogen;

an expansion chamber connected to said container to receive liquid cryogen therefrom;

a nozzle having an internal diameter between 0.010 inches and 0.045 inches;

first means to reduce the pressure in said expansion chamber to effect an increase in the flow of pressurized liquid cryogen into said chamber from said container and to change the flow of fluid from said chamber through said nozzle from single phase to dual phase with said nozzle having a diameter in the range of 0.010 inches to 0.021 inches; and second means to provide gas under pressure to said chamber to raise the pressure therein to approximate the pressure present when a smaller nozzle with a nozzle connected having a diameter in the range of 0.033 inches to 0.045 inches is connected in order to effect a flow of single phase gas through said nozzle, said flow changing from single phase to dual phase upon the substantial closing of said second means and the opening of said first means.

23. In a cryogenic device:

a container for liquid cryogen an expansion chamber connected to said container to receive liquid cryogen therefrom in which the entering cryogen vaporizes partially or totally to gas depending upon the pressure present;

a nozzle having an internal diameter in the range of 0.010 inches to 0.045 inches;

a source of gas under pressure connected to said expansion chamber to produce a suitable pressure in the chamber to limit the flow of cryogen into said expansion chamber from said container to produce a flow of single phase cryogen through a nozzle having an internal diameter greater than 0.021 inches;

first means operable to reduce the pressure in said expansion chamber to increase the flow of liquid cryogen from said container into said expansion chamber resulting in a change in the cryogen jetting from said container through said nozzle from single phase to dual phase flow with the nozzle connected to said chamber having a diameter in the range of 0.010 inches to 0.045 inches; and second means operable to stop the flow of pressurized gas into said expansion chamber from said source to cause the flow of cryogen through the nozzle to change from single phase flow to dual phase flow when the nozzle has a diameter greater than 0.021 inches.

* * * * *